US006229045B1

(12) United States Patent
Ringer et al.

(10) Patent No.: US 6,229,045 B1
(45) Date of Patent: *May 8, 2001

(54) PROCESS FOR PREPARING CARBOXYLIC ACIDS

(75) Inventors: James W. Ringer; Dennis A. Hucul; David C. Molzahn, all of Midland, MI (US)

(73) Assignee: Dow AgroSciences LLC, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/395,506

(22) Filed: Sep. 14, 1999

Related U.S. Application Data

(60) Provisional application No. 60/100,131, filed on Sep. 14, 1998.

(51) Int. Cl.$^7$ ................................................. C07C 51/00
(52) U.S. Cl. ......................... 562/526; 562/17; 562/523; 562/553; 562/566
(58) Field of Search .................................. 562/11, 16, 17, 562/523, 526, 538, 553, 566, 562, 563, 576; 502/244, 260

(56) References Cited

U.S. PATENT DOCUMENTS

| 4,130,711 | 12/1978 | Shier . |
|---|---|---|
| 4,153,581 | 5/1979 | Habermann . |
| 4,709,090 | 11/1987 | Nishibayashi et al. . |
| 4,782,183 | 11/1988 | Goto et al. . |
| 4,806,690 | 2/1989 | Bowman . |
| 5,220,054 | 6/1993 | Urano et al. . |
| 5,220,055 | 6/1993 | Urano et al. . |
| 5,225,592 | 7/1993 | Gomez et al. . |
| 5,367,112 | 11/1994 | Franczk et al. . |
| 5,689,000 | 11/1997 | Ebner et al. . |
| 5,739,390 | * 4/1998 | Franczyk et al. ..................... 562/526 |

FOREIGN PATENT DOCUMENTS

| 31694 | 7/1981 | (EP) . |
|---|---|---|
| 1447697 | 7/1966 | (FR) . |
| 09155195 | 7/1997 | (JP) . |

* cited by examiner

*Primary Examiner*—Jean F. Vollano
(74) *Attorney, Agent, or Firm*—Craig E. Mixan

(57) ABSTRACT

Aliphatic primary alcohols, including aliphatic primary alcohols possessing one or more oxygen, nitrogen and/or phosphorus heteroatoms that may be atoms substituting for carbon atoms in the alkyl group or component atoms of substituents on the alkyl group, were converted into salts of carboxylic acids by contacting an alkaline aqueous solution of the primary alcohol with a catalyst comprising cobalt, copper, and at least one of cerium, iron, zinc, and zirconium. Diethanolamine, for example, was converted to sodium iminodiacetate by treatment in an aqueous medium containing sodium hydroxide with a catalyst that was obtained by reducing a mixture of cobalt, copper, and zirconium oxides with hydrogen.

30 Claims, No Drawings

US 6,229,045 B1

PROCESS FOR PREPARING CARBOXYLIC ACIDS

RELATED U.S. APPLICATION DATA

Provisional application Ser. No. 60/100,131 filed Sep. 14, 1998.

BACKGROUND OF THE INVENTION

The present invention relates to the preparation of aliphatic carboxylic acids by the catalytic dehydrogenation of primary alcohols.

The preparation of carboxylic acids and salts of carboxylic acids using the corresponding primary alcohol as the starting material is often advantageous because the corresponding alcohols are often available and relatively inexpensive. The preparation of aliphatic carboxylic acids and their salts that possess oxygen, nitrogen and/or phosphorus heteroatoms, such as glycine, N-methylglycine, N-phosphonomethylglycine, iminodiacetic acid, N-phosphonomethyliminodiacetic acid, nitrilotriacetic acid, ethylenediaminetetraacetic acid, diglycolic acid, methoxyacetic acid, lactic acid, and the like, by such means is especially advantageous. These acids and their salts are valuable, for example, as intermediates for agricultural products and pharmaceuticals, as chelating agents, as animal feed additives, etc. Conversions of primary alcohols to their corresponding acids or to salts thereof have been carried out in the art by treatment of primary alcohols with a copper catalyst under conditions that lead to either dehydrogenation (U.S. Pat. Nos. 4,782,183, 5,220,054, 5,220,055, 5,292,936, 5,627,125, 5,689,000) or oxidation (U.S. Pat. No. 5,225, 592). Hydrogen is produced as a by-product in the dehydrogenation processes and water is produced as a by-product in the oxidation processes. Raney copper has typically been used as the catalyst.

Catalysts comprising cobalt, copper, and a third metal selected from iron, zinc, and zirconium and mixtures thereof, which can be made by reducing mixtures the corresponding metal oxides with hydrogen, are known from U.S. Pat. No. 4,153,581. These catalysts were disclosed in the art to be useful for the conversion of alcohols, aldehydes, and ketones to amines.

The discovery of improved processes and catalysts for converting primary aliphatic alcohols to carboxylic acids or their salts would be highly desirable.

SUMMARY OF THE INVENTION

It has now been found that aliphatic primary alcohol compounds, including aliphatic primary alcohols possessing one or more oxygen, nitrogen or phosphorus heteroatoms, which heteroatoms may be viewed as atoms substituting for carbon atoms in the alkyl group or component atoms of substituents on the alkyl group, can be converted into salts of carboxylic acid compounds by contacting the primary alcohol with a catalyst comprising cobalt, copper, and at least one additional metal selected from cerium, iron, zinc, and zirconium in an alkaline aqueous medium.

The invention includes a process for preparing a salt of an aliphatic carboxylic acid compound that is unsubstituted or possesses one or more substituents that contain one or more oxygen, nitrogen and/or phosphorus atoms, which process comprises contacting a primary aliphatic alcohol compound that is unsubstituted or possesses one or more substituents that contain one or more oxygen, nitrogen and/or phosphorus atoms with a catalyst comprising, on a contained metals basis, about 10 to about 90 mole percent cobalt, about 8 to about 88 mole percent copper, and about 1 to about 16 mole percent of a third metal selected from cerium, iron, zinc, and zirconium, or mixtures thereof, in an alkaline aqueous medium, in the effective absence of oxygen, and at a temperature of about 120° C. to about 200° C.

The salts of aliphatic carboxylic acids obtained in the process can be converted to the corresponding aliphatic carboxylic acids by acidification with a strong acid using methods well established in the art.

The process of the invention is often preferably used to convert aliphatic primary alcohol compounds possessing substituents containing one or more oxygen, nitrogen and/or phosphorus heteroatoms to the corresponding carboxylic acid compounds or their salts. The conversion of optionally N-substituted 2-aminoethanol and 2-aminopropanol compounds and optionally mono-O-substituted 1,2-ethanediol (ethylene glycol) and 1,2-propanediol (propylene glycol) compounds (substituents on the 2-hydroxyl in the latter) is often preferred. The conversion of diethanolamine to iminodiacetic acid or an alkali metal salt of iminodiacetic acid, of ethanolamine to glycine or an alkali metal salt of glycine, of N-methylethanolamine to sarcosine or an alkali metal salt of sarcosine, of N-phosphonomethylethanolamine to N-phosphonomethylglycine or an alkali metal salt of N-phosphonomethylglycine, and of N-phosphonomethyldiethanolamine to N-phosphonomethyliminodiacetic acid or an alkali metal salt of N-phosphonomethyliminodiacetic acid are often, independently, of special interest.

Catalysts containing about 30 to about 50 mole percent cobalt, about 45 to about 65 mole percent copper, and about 3 to about 10 mole percent of the third metal, on the basis of the total metal content, are generally most preferred. Zirconium is often a preferred third metal.

It is often preferred to carry out the process at about 140° C. to about 200° C.

It is usually preferred to carry out the reaction in an aqueous medium containing an alkali metal hydroxide compound in the amount of at least about one mole to about 2 moles per mole of primary alcohol moiety undergoing conversion to carboxylic acid group. Sodium hydroxide is often preferred as the alkali metal hydroxide compound.

DETAILED DESCRIPTION OF THE INVENTION

The process of the present invention involves the catalytic dehydrogenation of aliphatic primary alcohol compounds, including aliphatic primary alcohol compounds possessing oxygen, nitrogen and/or phosphorus heteroatoms, to obtain salts of carboxylic acids. This dehydrogenation reaction can be illustrated by the following equation:

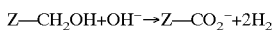

$$Z\text{—}CH_2OH + OH^- \rightarrow Z\text{—}CO_2^- + 2H_2$$

wherein Z is an alkyl group that optionally possesses one or more oxygen, nitrogen and/or phosphorus containing substituents.

The salts of carboxylic acids obtained in the dehydrogenation reaction can be converted to the corresponding acids by acidification with a strong acid according to the equation:

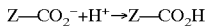

$$Z\text{—}CO_2^- + H^+ \rightarrow Z\text{—}CO_2H$$

Suitable acids include mineral acids such as hydrochloric acid, hydrobromic acid, sulfuric acid, and phosphoric acid and other strong acids such as trifluoroacetic acid, benzenesulfonic acid, and the like. Suitable acids generally have a p$K_a$ of about 5 or less. Acidification of the reaction mixture produced in the dehydrogenation to obtain the corresponding carboxylic acids is an optional second step in the process. Thus, the process of the invention can be used to prepare either aliphatic carboxylic acids or their salts.

The salts and acids prepared in the process of the invention can be recovered by conventional means, if desired.

A broad variety of aliphatic primary alcohol compounds are suitable starting materials in the process. Importantly, these alcohol compounds may possess oxygen, nitrogen and/or phosphorus heteroatoms. Primary aliphatic alcohols possessing one or more oxygen or nitrogen containing substituents are often preferred. The process works best when applied to aliphatic primary alcohols that are essentially soluble in the alkaline aqueous medium used under the reaction conditions employed.

The process of the invention is especially useful for the preparation of aliphatic carboxylic acids of Formula II or salts thereof from aliphatic primary alcohols of Formula I:

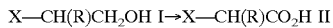

X—CH(R)CH$_2$OH I→X—CH(R)CO$_2$H II wherein

X represents H, CH$_3$, OH, O(C$_1$–C$_4$)alkyl, OCH(R)CH(R)OH, OCH(R)CO$_2$H, OCH(R)CH(R)NH$_2$, OCH(R)CH(R)—NH(C$_1$–C$_4$)alkyl, OCH(R)CH(R)N((C$_1$–C$_4$)alkyl)$_2$, OCH(R)CH(R)—N(CH(R)CH$_2$OH)$_2$, OCH(R)CH(R)N(CH(R)CO$_2$H)$_2$, NH$_2$, NH(C$_1$–C$_4$)alkyl, NHCH$_2$P(O)(OH)$_2$, N((C$_1$–C$_4$)alkyl)$_2$, NHCH(R)CH(R)OH, N(CH(R)CH(R)OH)$_2$, NHCH(R)CO$_2$H, N(CH(R)CO$_2$H)$_2$, N(C$_1$–C$_4$)alkyl) (CH(R)CH(R)OH), N(CH(R)CH(R)OH)(CH$_2$P(O)(OH)$_2$), N(CH(R)CO$_2$H)(CH$_2$P(O)(OH)$_2$), N(C$_1$–C$_4$)alkyl) (CH(R)CO$_2$H), N(CH(R)CH(R)OH)(CH(R)CO$_2$H), N(CH$_2$CH$_2$OH)CH$_2$CH$_2$N(CH$_2$CH$_2$OH)$_2$, or N(CH$_2$CH$_2$OH)CH$_2$CH$_2$N(CH$_2$CH$_2$OH)N(CH$_2$CH$_2$OH)$_2$; and each R independently represents H or CH$_3$.

The aliphatic primary alcohols of Formula I can viewed as optionally N-substituted 2-aminoethanol and 2-aminopropanol and optionally mono-O-substituted 2-hydroxyethanol and 2-hydroxypropanol compounds (substituents on the 2-hydroxy oxygen), the optional substituents being alkyl moieties optionally possessing oxygen and nitrogen atom containing functionality.

The term alkyl as used herein includes straight chain, branched chain, and cyclic alkyl groups. Examples include methyl, ethyl, propyl, butyl, 1-methylethyl, 2-methylbutyl, cyclopropyl, and the like.

R in Formulas I and II is usually preferably H. Primary alcohol compounds of Formula I wherein R represents H can generally be considered to be 2-hydroxyethyl derivatives of water, alcohols, ammonia, and amines and the process of the invention using them as starting materials can be considered to involve the conversion of hydroxyethyl moieties to acetic acid moieties. Ethanolamine, 2-aminopropanol, N-methylethanolamine, N-phosphonomethylethanolamine, diethanolamine, N-methyldiethanolamine, N-phosphonomethyldiethanolamine, N-(2-hydroxyethyl)glycine, N,N-di(2-hydroxyethyl)glycine, N,N-di(2-hydroxyethyl)alanine, triethanolamine, 2-(2-aminoethoxy)ethanol, diethylene glycol, N-(2-(2-hydroxyethoxy)ethyl)diethanolamine, N-(2-(2-hydroxyethoxy)ethyl)iminodiacetic acid, and N,N,N',N'-tetra(2-hydroxyethyl)ethylenediamine are examples of starting materials that are often, independently, preferred. Ethanolamine, N-methylethanolamine, N-phosphonomethylethanolamine, diethanolamine, and N-phosphonomethyldiethanolamine are, independently, often primary alcohols of special interest.

The primary aliphatic alcohol compound starting materials of the invention described above may contain more than one primary alcohol function. The process of the invention generally converts each primary alcohol function present to a carboxylic acid function or to a salt thereof. Thus, generally, diethylene glycol is converted to diglycolic acid, diethanolamine is converted to iminodiacetic acid, and triethanolamine is converted to nitrilotriacetic acid. When multiple primary alcohol functions are present, however, substantial quantities of products wherein less than all of them have been converted to carboxylic acid functions can be obtained by stopping the reaction before completion. Thus, for example, substantial amounts of (2-hydroxyethoxy)acetic acid can be obtained from diethylene glycol and substantial amounts of (2-hydroxyethylamino)acetic acid can be obtained from diethanolamine. The preparation of compounds which possess multiple carboxylic acid moieties and at least one nitrogen atom and which are effective chelating agents for cobalt is sometimes complicated by the extraction of cobalt from the catalyst. Secondary and tertiary alcohol functional groups present in a starting material primary alcohol remain unchanged in the process. Thus, for example, 1,2-propanediol is converted to lactic acid.

The process of the invention can be used, for example, for the conversion of ethanolamine to glycine or an alkali metal salt of glycine, 2-aminopropanol to 2-aminopropanoic acid (alanine) or an alkali metal salt of alanine, N-methylethanolamine to N-methylglycine (sarcosine) or an alkali metal salt of sarcosine, N-phosphonomethylethanolamine to N-phosphonomethylglycine or an alkali metal salt of N-phosphonomethylglycine, diethanolamine or N-(2-hydroxyethyl)glycine to iminodiacetic acid or an alkali metal salt of iminodiacetic acid, N-methyldiethanolamine or N-methyl(2-hydroxyethyl)glycine to N-methyliminodiacetic acid or an alkali metal salt of N-methyliminodiacetic acid, N-phosphonomethyldiethanolamine or N-phosphonomethyl(2-hydroxyethyl)glycine to N-phosphonomethyliminodiacetic acid or an alkali metal salt of N-phosphonomethyliminodiacetic acid, triethanolamine, N,N-di(2-hydroxyethyl)glycine, or N-(2-hydroxyethyl)iminodiacetic acid to nitrilotriacetic acid or an alkali metal salt of nitrilotriacetic acid, N,N-di(2-hydroxyethyl)alanine to N,N-di(carboxymethyl)alanine or an alkali metal salt of N,N-di(carboxymethyl)alanine, 2-(2-aminoethoxy)ethanol to (2-aminoethoxy)acetic acid or an alkali metal salt of (2-aminoethoxy)acetic acid, diethylene glycol to diglycolic acid or an alkali metal salt of diglycolic acid, 1,2-propanediol to lactic acid or an alkali metal salt of lactic acid, N-(2-(2-hydroxyethoxy)ethyl)iminodiacetic acid or N-(2-(2-hydroxyethoxy)ethyl)diethanolamine to N-(2-(carboxymethoxy)ethyl)iminodiacetic acid or an alkali metal salt of N-(2-(carboxymethoxy)ethyl)iminodiacetic acid, N,N,N',N'-tetra(2-hydroxyethyl)ethylenediamine to ethylenediaminetetraacetic acid or an alkali metal salt of ethylenediaminetetraacetic acid, or N,N,N',N",N"-penta(2-hydroxyethyl)diethylenetriamine to diethylenetriaminepentaacetic acid or an alkali metal salt of diethylenetriaminepentaacetic acid, each conversion being independently preferred in appropriate circumstances. The conversion of diethanolamine to iminodiacetic acid or an alkali metal salt of iminodiacetic acid, of ethanolamine to glycine or an alkali metal salt of glycine, of N-methylethanolamine to sarcosine or an alkali metal salt of sarcosine, of N-phosphonomethylethanolamine to N-phosphonomethylglycine or an alkali metal salt of N-phosphonomethylglycine, and of N-phosphonomethyldiethanolamine to N-phosphonomethyliminodiacetic acid or an alkali metal salt of N-phosphonomethyliminodiacetic acid are often, independently, of special interest.

Catalysts that are suitable for the process contain both cobalt and copper as required components. A third component, which is also required, can be selected from zirconium, iron, zinc, and cerium and mixtures of these metals. Catalysts containing about 10 to about 90 mole percent cobalt, about 8 to about 88 mole percent copper, and about 1 to about 16 mole percent of the third required component on the basis of the total metal content work well. Catalysts containing about 20 to about 90 mole percent cobalt, about 8 to about 72 mole percent copper, and about 1 to about 16 mole percent of the third required component are often preferred. Catalysts containing about 25 to about 70 mole percent cobalt, about 25 to about 70 mole percent copper, and about 2 to about 14 mole percent of the third component are often more preferred and catalysts containing about 30 to about 50 mole percent cobalt, about 45 to about 65 mole percent copper, and about 3 to about 10 mole percent of the third component are generally most preferred.

Zirconium is often preferred as the third component metal.

Quantities less than 1 mole percent based on the total metal content of the catalyst of additional metals are generally not substantially deleterious to the process. Thus, for example, small amounts of metals such as nickel, chromium, and tungsten can be tolerated.

The catalysts used in the invention can be prepared by any of the methods disclosed in U.S. Pat. NO. 4,153,581, hereby incorporated by reference, and related methods. Suitable catalysts, for example, can be prepared by first heating a mixture of the carbonates of cobalt, copper, and one or more of iron, zirconium, zinc and cerium to drive off carbon dioxide and obtain a mixture of the corresponding oxides and then activating the mixed oxide product obtained by heating it in a hydrogen atmosphere at a temperature of about 150° C. to 250° C. The reduction takes place in about 1 to about 24 hours, typically in about 6 to 7 hours. Higher temperatures do not appear to be deleterious.

The mixture of oxides used in the preparation of the catalyst is generally in the form of a powder or of a pellet prepared from the powder. Pellets can be formed from the powder in any of the ways known in the art, such as by compression molding, and may contain a binder, such as graphite, and/or a lubricant, such as a fatty acid. Pellets of about 0.1 cm to about 1.0 cm height and about 0.1 cm to about 1.0 cm diameter are typically employed in fixed bed reactors. Powder and other small particle forms of the catalyst are generally employed in stirred reactors.

The catalysts used in the invention may additionally contain support or carrier components, such as carbon, silicon carbide, and some clays. These components can be mixed with the catalyst prepared as above or can be added to the mixture of oxides used to prepare the catalyst before reduction. It is often preferred to use catalysts that do not contain support or carrier components.

After preparation, the catalysts are best protected from exposure to air. Catalysts that have been exposed to air, however, can be reactivated by heating in an hydrogen atmosphere before use.

The amount of catalyst used in the process is an amount that causes the desired reaction to take place in a convenient amount of time; that is, an amount that provides a convenient reaction rate. The amount of catalyst that provides a convenient reaction rate varies depending on such catalyst parameters as the precise composition, the particle size, the amount of surface area, and the size and volume of the surface pores. It also varies depending on the type and geometry of the reactor used, whether a batch or continuous operating mode is used, the identity of the starting material, the identity of the desired product, the medium used, the temperature, the agitation efficiency, and other operational factors. A suitable amount of catalyst for each situation can be readily determined by simple testing using methods well established in the art.

The process of the invention is carried out in an aqueous alkaline medium; that is, in a medium containing water and having a pH greater than 7. The reagent that makes the medium alkaline can be any of the known reagents that do not adversely react under the process conditions. Suitable reagents include, metal hydroxides, metal oxides, metal carbonates, and the like. Alkali metal hydroxides are generally preferred. Sodium and potassium hydroxide are generally more preferred and sodium hydroxide is typically most preferred. The alkaline reagent can be added in any form. Typically, undiluted reagent or an aqueous solution of the reagent is used.

The amount of alkaline reagent used is sufficient to maintain an alkaline aqueous medium throughout the reaction. Generally, at least about one mole to about 2 molar equivalents of alkaline reagent are used per mole of primary alcohol moiety undergoing conversion to carboxylic acid group. This amount is sufficient to convert all of the carboxylic acid functionality produced into a salt form and to maintain a pH of greater than 7 throughout the dehydrogenation reaction.

Organic solvents that are water-soluble and are not reactive under the reaction conditions can be present in the reaction medium. Suitable organic solvents include 1,2-dimethoxyethane, dioxane, tetrahydrofuran, and 2-propanol.

The dehydrogenation reaction takes place well at temperatures between about 120° C. to about 200° C. It is often preferred to carry out the process at about 140° C. to about 200° C. Pressure does not appear to be an important variable in reaction and the reaction can be carried out under the pressure generated by the aqueous medium and hydrogen at the reaction conditions used. It is often, however, convenient and advantageous to release some of the hydrogen formed during the reaction to keep the pressure below about 1000 pounds per square inch (psi) (68,900 kilopascals (kPa)) and more preferable to control the pressure to below about 700 psi (48,230 kPa). In other situations, it is more preferable to control the pressure to below about 350 psi (24,130 kPa). It is often most preferable to carry out the process at a pressure of about 200 psi (13,800 kPa) to about 300 psi (20,670 kPa).

The dehydrogenation reaction of the present invention can be carried out in either a batch or a continuous manner. When operating in a batch mode in a single reactor or in a continuous mode in a series of continuous stirred tank reactors, it is advantageous to provide good agitation. When fixed bed type reactors are used, it is generally desired to provide for turbulent flow of the reaction mixture through the reactor. When operating in the batch mode, the reaction is generally continued until most or all of the starting primary alcohol has reacted. When the reaction is carried out in a continuous mode, the flow rate and other parameters are generally adjusted so that most or all of the starting primary alcohol has been reacted when the reaction mixture exits the reactor or series of reactors.

Reactors constructed of corrosion resistant metals, such as copper, nickel, Hastalloy C, and Monel, are generally preferred.

The following examples are presented to illustrate various aspects of the invention. They should not be construed as limiting the scope of the invention.

EXAMPLES

1. Disodium Iminodiacetate from Diethanolamine

A stirred Hastalloy C metal Parr pressure reactor was charged with 51 g (grams) (0.49 mol (moles)) of diethanolamine, 82 g of 50 percent solution in water (1.03 mol) of sodium hydroxide, and 68 g of water. To this was added 10.0 g of a catalyst containing, on a mole percent of metals basis, 38 percent cobalt, 57 percent copper, and 5 percent zirconium, which catalyst was prepared by reducing a mixture of cobalt oxide, copper oxide, and zirconium oxide (obtained by heating a mixture of the corresponding carbonates) and activated by treatment with a 10 percent hydrogen/90 percent nitrogen stream at 200° C. for 16 hours. The catalyst was in the form of a fine powder. The mixture was heated to 160° C. with stirring. The hydrogen, which began to evolve at about 140° C., was vented off two or three times to keep the pressure below about 700 psi (48,230 kPa). After 40–45 min, hydrogen evolution ceased and the mixture was cooled and analyzed by high pressure liquid chromatography. The conversion of diethanolamine to disodium iminodiacetate was found to be 97 to 100 percent complete.

2. Disodium Iminodiacetate from Diethanolamine

Example 1 was repeated except that only 2.0 g of catalyst were used. Hydrogen evolution ceased after about 250 min and the conversion of diethanolamine to disodium iminodiacetate was found to be 97 to 100 percent complete.

3. Disodium Iminodiacetate from Diethanolamine

Example 1 was repeated except that the catalyst used was recovered from a previous experiment using the procedure of Example 1. Hydrogen evolution ceased after about 50 min and the conversion of diethanolamine to disodium iminodiacetate was found to be 97 to 100 percent complete.

4. Disodium Iminodiacetate from Diethanolamine

Example 1 was repeated except that the catalyst contained 5 percent cerium in place of zirconium. Hydrogen evolution ceased after about 100 min and the conversion of diethanolamine to disodium iminodiacetate was found to be 97 to 100 percent complete.

5. Sodium (2-Aminoethoxy)acetate from 2-(2-Aminoethoxy)ethanol

A stirred Hastalloy C metal Parr pressure reactor was charged with 49.5 g (0.47 mol) of 2-(2-aminoethoxy) ethanol, 82 g of 50 percent solution in water (1.03 mol) of sodium hydroxide, and 68 g of water. To this was added 10.0 g of a catalyst containing, on a mole percent of metals basis, 38 percent cobalt, 57 percent copper, and 5 percent zirconium prepared as in Example 1. The mixture was heated to 170° C. with stirring. The hydrogen, which began to evolve at about 140° C., was vented off one or two times to keep the pressure below about 700 psi (48,230 kPa). After 560 min, hydrogen evolution ceased and the mixture was cooled and analyzed by proton nuclear magnetic resonance spectroscopy. The conversion of 2-(2-aminoethoxy)ethanol to sodium (2-aminoethoxy)acetate was found to be 80–90 percent complete.

6. Sodium Lactate from 1,2-Propanediol

A stirred Hastalloy C metal Parr pressure reactor was charged with 28.2 g (0.37 mol) of 1,2-propanediol (propylene glycol), 32.6 g of 50 percent aqueous solution (0.41 mol) of sodium hydroxide, and 115 g of water. To this was added 1.6 g of a catalyst containing, on a mole percent of metals basis, 38 percent cobalt, 57 percent copper, and 5 percent zirconium prepared as in Example 1. The reactor was purged three times with nitrogen and was then heated with stirring to 180° C. After 250 min, the mixture was cooled and analyzed by $^{13}C$ nuclear magnetic resonance. Conversion of the 1,2-propanediol was complete and over 98 percent of the product was identified as sodium lactate.

7. Sodium Acetate from Ethanol

A stirred Hastalloy C metal Parr pressure reactor was charged with 11.1 g (0.24 mol) of ethanol, 20 g of 50 percent aqueous solution (0.25 mol) of sodium hydroxide, and 70 g of water. To this was added 1.0 g of a catalyst containing, on a mole percent of metals basis, 38 percent cobalt, 57 percent copper, and 5 percent zirconium prepared as in Example 1. The reactor was purged three times with nitrogen and was then heated with stirring to 160° C. The pressure stopped rising after about 200 min. After 600 min, the mixture was cooled and analyzed by $^{13}C$ nuclear magnetic resonance. Conversion of the ethanol was about 35 percent complete and the primary product was identified as sodium acetate.

8. Tetrasodium Ethylenediaminetetraacetate from N, N,N',N'-tetra(2-hydroxyethyl)ethylenediamine A stirred Hastalloy C metal Parr pressure reactor was charged with 18.5 g of N,N,N',N'-tetra(2-hydroxyethyl) ethylenediamine, 26.9 g of 50 percent aqueous solution of sodium hydroxide, and 80 g of water. To this was added 1.0 g of a catalyst containing, on a mole percent of metals basis, 38 percent cobalt, 57 percent copper, and 5 percent zirconium prepared as in Example 1. The reactor was purged three times with nitrogen and was then heated with stirring to 160° C. After 1350 min, another 1.0 g of catalyst was added. After another 1350 min, the mixture was cooled and analyzed by $^{13}C$ nuclear magnetic resonance. The solution was pink to purple in color. Conversion of the N,N,N',N'-tetra(2-hydroxyethyl)ethylenediamine appeared to be complete and the primary product appeared to be tetrasodium ethylenediaminetetraacetate.

9. Disodium Diglycolate from Diethylene Glycol

A 15 weight percent diethylene glycol solution in water containing a 2.1 to 1 mole ratio of sodium hydroxide to diethylene glycol was prepared. A 14 inch (35.5 cm)×0.5 inch (1.27 cm) fixed bed, column reactor made of Hastalloy C and equipped with a back pressure regulator was filled with 28 g of a catalyst containing, on a mole percent of metals basis, 38 percent cobalt, 57 percent copper, and 5 percent zirconium prepared by reducing a mixture of cobalt oxide, copper oxide, and zirconium oxide (obtained by heating a mixture of the corresponding carbonates) and activated by treatment with a 10 percent hydrogen/90 percent nitrogen stream at 200° C. for 16 hours. The catalyst was in the form of about 0.19 inch (0.48 cm (centimeter)) diameter and about 0.19 inch (0.48 cm) height pellets prepared by pelletizing the mixture of oxides before reduction. The catalyst was mixed with about 30 g of silicon carbide fines of about 200 micron diameter to fill out the reactor for even liquid flow. The reactor was heated to 160° C. by means of a stainless steel jacket filled with recirculating oil and the diethylene glycol solution was passed through top to bottom at the rate of 1.0 mL (milliliter) per min at a pressure of 300 psig (21,700 kPa). The effluent was analyzed by $^{13}$C nuclear magnetic resonance and found to contain about 52 mole percent disodium diglycolate, 37 percent sodium (2-hydroxyethoxy)acetate, and 11 percent diethylene glycol.

10. Sodium N-Methylglycinate from N-Methylethanolamine

A 15 weight percent N-methylethanolamine solution in water containing a 1.1 to 1 mole ratio of sodium hydroxide to N-methylethanolamine was prepared by combining 150 g of N-methylethanolamine, 176 g of 50 percent aqueous sodium hydroxide, and 674 g of water. This solution was passed through the fixed bed reactor and catalyst of Example 9 top to bottom at the rate of 0.5 mL and 1.0 mL per min at 160° C. and 300 psig (21,700 kPa) pressure. The reaction was determined by $^{13}$C nuclear magnetic resonance to have proceeded with complete conversion of the N-methylethanolamine at 0.5 mL per min and with 90 percent conversion at 1.0 mL per min producing, in both cases, sodium N-methylglycinate (sodium salt of sarcosine) as the only product.

11. Dehydrogenation of Triethanolamine

A 14.4 weight percent triethanolamine solution in water containing a 3.1 to 1 mole ratio of sodium hydroxide to triethanolamine was prepared and was passed at the rate of 0.5 mL per min through the fixed bed reactor and catalyst of Example 9 top to bottom at 160° C. and 300 psig (21,700 kPa) pressure. The effluent, which was pink, was analyzed by $^{13}$C nuclear magnetic resonance and found to contain 18 mole percent unreacted triethanolamine, 35 mole percent sodium N,N-di(2-hydroxyethyl)glycinate, 37 mole percent disodium N-(2-hydroxyethyl)iminodiacetate, and 10 mole percent nitrilotriacetic acid.

12. Sodium Iminodiacetate from Diethanolamine

A 15 weight percent diethanolamine solution in water containing a 2.1 to 1 mole ratio of sodium hydroxide to diethanolamine was prepared. The reactor and catalyst system of Example 9 was heated to 160° C. and the diethanolamine solution was passed through top to bottom at the rate of 1.0 mL per min at a pressure of 300 psig (21,700 kPa). The effluent was analyzed by $^{13}$C nuclear magnetic resonance and found to contain about 87 mole percent disodium iminodiacetate, 8 mole percent sodium (2-hydroxyethyl) glycinate, and 5 mole percent diethanolamine.

A 25 weight percent diethanolamine solution in water containing a 2.1 to 1 mole ratio of sodium hydroxide to diethanolamine was prepared by combining 872 g of diethanolamine, 1395 g of 50 percent aqueous sodium hydroxide, and 1220 g of water. This solution was passed through the same reactor under the same reaction conditions. The effluent was analyzed by $^{13}$C nuclear magnetic resonance and found to contain about 77 mole percent disodium iminodiacetate, 11 mole percent sodium (2-hydroxyethyl) glycinate, and 12 mole percent diethanolamine.

13. Sodium Glycinate from Ethanolamine

A 15 weight percent ethanolamine solution in water containing a 1.1 to 1 mole ratio of sodium hydroxide to ethanolamine was prepared by combining 75 g of ethanolamine, 108 g of 50 percent aqueous sodium hydroxide, and 318 g of water. The reactor and catalyst system of Example 9 was heated to 160° C. and the ethanol-amine solution was passed through top to bottom at the rate of 1.0 mL per min at a pressure of 300 psig (21,700 kPa). The effluent was analyzed by $^{13}$C nuclear magnetic resonance and found to contain about 95 mole percent sodium glycinate and 5 mole percent ethanolamine.

14. Trisodium N-Phosphonomethylglycinate from Disodium N-Phosphonomethylethanolamine The disodium salt of N-phosphonomethylethanolamine (30 g; 0.15 mol) was dissolved in 192 g of water and a slight stoichiometric excess of 50 weight percent NaOH (13.3 g; 0.17 mol) was added to maintain alkalinity. A 24 inch (60.96 cm)×0.5 inch (1.27 cm) fixed bed, column reactor made of Hastalloy C and equipped with a back pressure regulator was filled with 25 g of silicon carbide (80 grit), 20 g of ⅛ inch (3.175 mm (millimeters)) pellets containing, on a mole percent of metals basis, 38 percent cobalt, 57 percent copper, and 5 percent zirconium, in which the interstitial spaces between the pellets were filled with 20 g of silicon carbide fines, and an additional 20 g of silicon carbide fines at the top of the column. The catalyst was activated by treatment with a 10 percent hydrogen/90 percent nitrogen stream at 200° C. for 16 hours. The reactor was heated to 160° C. by means of a stainless steel jacket filled with recirculating oil and the alkaline feed solution was passed through top to bottom at the rate of 0.8 mL per min while the pressure was controlled at or just below 300 psig (21,700 kPa) by venting hydrogen gas. The effluent was analyzed by $^{13}$C NMR and gas chromatography/mass spectrometry (GC/mass spec). Conversion of disodium N-phosphonomethylethanolamine to trisodium N-phosphonomethylglycinate was about 90 percent.

15. Tetrasodium N-Phosphonomethyliminodiacetate from Disodium N-Phosphonomethyldiethanolamine The procedure of Example 14 was repeated using a feed consisting of the disodium salt of N-phosphonomethyldiethanolamine (20 g; 0.08 mol) dissolved in 171 g of water and 50 weight percent NaOH (9.1 g; 0.11 mol). The effluent was analyzed by $^{13}$C NMR and GC/mass spec and was found to contain about 60 percent tetrasodium N-phosphonomethyliminodiacetate, 32 percent trisodium N-phosphonomethyl-N-hydroxyethylglycinate and 8 percent disodium N-phosphonomethyldiethanolamine.

What is claimed is:

1. A process for the preparation of a salt of an aliphatic carboxylic acid compound that contains nitrogen and optionally contains oxygen and/or phosphorus atoms, which process comprises contacting a primary aliphatic alcohol compound that contains nitrogen and optionally contains oxygen and/or phosphorus atoms with a catalyst, obtained by heating a mixture of metal oxides in a hydrogen atmosphere, comprising, on a contained metals basis, about 20 to about 90 mole percent cobalt, about 8 to about 72 mole percent copper, and about 1 to about 16 mole percent of a third metal selected from cerium, iron, zinc, and zirconium, or mixtures thereof, in an alkaline aqueous medium, in the effective absence of oxygen, and at a temperature of about 120° C. to about 200° C.

2. A process according to claim 1 wherein the alcohol compound contains nitrogen and optionally contains oxygen atoms.

3. A process according to claim 1 wherein the alcohol compound has the formula:

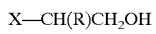

wherein

X represents OCH(R)CH(R)NH$_2$, OCH(R)CH(R)NH (C$_1$–C$_4$)alkyl, OCH(R)CH(R)N((C$_1$–C$_4$)alkyl)$_2$, OCH (R)CH(R)N(CH(R)CH$_2$OH)$_2$, OCH(R)CH(R)N(CH (R)CO$_2$H)$_2$, NH$_2$, NH(C$_1$–C$_4$)alkyl, NHCH$_2$P(O) (OH)$_2$, N((C$_1$–C$_4$)alkyl)$_2$, NHCH(R)CH(R)OH, N(CH (R)CH(R)OH)$_2$, NHCH(R)CO$_2$H, N(CH(R)CO$_2$H)$_2$, N(C$_1$–C$_4$)alkyl)(CH(R)CH(R)OH), N(CH(R)CH(R) OH)(CH$_2$P(O)(OH)$_2$), N(CH(R)CO$_2$H)(CH$_2$P(O) (OH)$_2$), N(C$_1$–C$_4$)alkyl)(CH(R)CO$_2$H), N(CH(R)CH (R)OH)(CH(R)CO$_2$H), N(CH$_2$CH$_2$OH)CH$_2$CH$_2$N (CH$_2$CH$_2$OH)$_2$, or N(CH$_2$CH$_2$OH)CH$_2$CH$_2$N (CH$_2$CH$_2$OH)N(CH$_2$CH$_2$OH)$_2$; and each R independently represents H or CH$_3$.

4. A process according to claim 1 wherein the alcohol compound is selected from ethanolamine, 2-aminopropanol, N-methylethanolamine, N-phosphonomethyl-ethanolamine, diethanolamine, N-methyldiethanolamine, N-phosphonomethyldiethanolamine, N-(2-hydroxyethyl) glycine, N,N-di(2-hydroxyethyl)glycine, N,N-di(2-hydroxyethyl)alanine, triethanolamine, 2-(2-aminoethoxy) ethanol, N-(2-(2-hydroxyethoxy)ethyl)diethanolamine, N-(2-(2-hydroxyethoxy)ethyl)iminodiacetic acid, and N,N, N',N'-tetra(2-hydroxyethyl)ethylenediamine.

5. A process according to claim 4 wherein the alcohol compound is diethanolamine and the compound prepared is a salt of iminodiacetic acid.

6. A process according to claim 4 wherein the alcohol compound is ethanolamine and the compound prepared is a salt of glycine.

7. A process according to claim 1 wherein the catalyst contains about 25 to about 70 mole percent cobalt, about 25 to about 70 mole percent copper, and about 2 to about 14 mole percent of the third metal, on the basis of the total metal content.

8. A process according to claim 7 wherein the catalyst contains about 30 to about 50 mole percent cobalt, about 45 to about 65 mole percent copper, and about 3 to about 10 mole percent of the third metal, on the basis of the total metal content.

9. A process according to claim 1 wherein the third metal is zirconium.

10. A process according to claim 9 wherein the catalyst comprises about 38 mole percent cobalt, about 57 mole percent copper, and about 5 mole percent zirconium on the basis of the total metal content.

11. A process according to claim 1 wherein the temperature is maintained at about 140° C. to about 200° C.

12. A process according to claim 1 wherein the medium contains an alkali metal hydroxide in the amount of at least about one mole to about 2 moles per mole of primary alcohol moiety undergoing conversion to carboxylic acid group.

13. A process according to claim 1 wherein the alkali metal hydroxide is sodium hydroxide.

14. A process according to claim 1 carried out in a batch reactor system.

15. A process according to claim 1 carried out in a continuous reactor system.

16. A process for the preparation of an aliphatic carboxylic acid compound that contains nitrogen and optionally contains oxygen and/or phosphorus atoms, which process comprises contacting a primary aliphatic alcohol compound that contains nitrogen and optionally contains oxygen and/or phosphorus atoms with a catalyst, obtained by heating a mixture of metal oxides in a hydrogen atmosphere, comprising, on a contained metals basis, about 20 to about 90 mole percent cobalt, about 8 to about 72 mole percent copper, and about 1 to about 16 mole percent of a third metal selected from cerium, iron, zinc, and zirconium, or mixtures thereof, in an alkaline aqueous medium, in the effective absence of oxygen, and at a temperature of about 120° C. to about 200° C., and, thereafter acidifying with a strong acid.

17. A process according to claim 16 wherein the alcohol compound contains nitrogen and optionally contains oxygen atoms.

18. A process according to claim 16 wherein the alcohol compound has the formula:

wherein

X represents OCH(R)CH(R)NH$_2$, OCH(R)CH(R)NH (C$_1$–C$_4$)alkyl, OCH(R)CH(R)N((C$_1$–C$_4$)alkyl)$_2$, OCH (R)CH(R)N(CH(R)CH$_2$OH)$_2$, OCH(R)CH(R)N(CH (R)CO$_2$H)$_2$, NH$_2$, NH(C$_1$–C$_4$)alkyl, NHCH$_2$P(O) (OH)$_2$, N((C$_1$–C$_4$)alkyl)$_2$, NHCH(R)CH(R)OH, N(CH (R)CH(R)OH)$_2$, NHCH(R)CO$_2$H, N(CH(R)CO$_2$H)$_2$, N(C$_1$–C$_4$)alkyl)(CH(R)CH(R)OH), N(CH(R)CH(R) OH)(CH$_2$P(O)(OH)$_2$), N(CH(R)CO$_2$H)(CH$_2$P(O) (OH)$_2$), N(C$_1$–C$_4$)alkyl)(CH(R)CO$_2$H), N(CH(R)CH (R)OH)(CH(R)CO$_2$H), N(CH$_2$CH$_2$OH)CH$_2$CH$_2$N (CH$_2$CH$_2$OH)$_2$, or N(CH$_2$CH$_2$OH)CH$_2$CH$_2$N (CH$_2$CH$_2$OH)N(CH$_2$CH$_2$OH)$_2$; and each R independently represents H or CH$_3$.

19. A process according to claim 16 wherein the alcohol compound is selected from ethanolamine, 2-aminopropanol, N-methylethanolamine, N-phosphono-methylethanolamine, diethanolamine, N-methyldiethanolamine, N-phosphonomethyldiethanolamine, N-(2-hydroxyethyl) glycine, N,N-di(2-hydroxyethyl)glycine, N,N-di(2-hydroxyethyl)alanine, triethanolamine, 2-(2-aminoethoxy) ethanol, N-(2-(2-hydroxyethoxy)ethyl)diethanolamine, N-(2-(2-hydroxyethoxy)ethyl)iminodiacetic acid, and N,N, N',N'-tetra(2-hydroxyethyl)ethylenediamine.

20. A process according to claim 19 wherein the alcohol compound is diethanolamine and the compound prepared is iminodiacetic acid.

21. A process according to claim 19 wherein the alcohol compound is ethanolamine and the compound prepared is glycine.

22. A process according to claim 16 wherein the catalyst contains about 30 to about 50 mole percent cobalt, about 45 to about 65 mole percent copper, and about 3 to about 10 mole percent of the third metal, on the basis of the total metal content.

23. A process according to claim 16 wherein the third metal is zirconium.

24. A process according to claim 23 wherein the catalyst comprises about 38 mole percent cobalt, about 57 mole percent copper, and about 5 mole percent zirconium on the basis of the total metal content.

25. A process according to claim 16 wherein the temperature is maintained at about 140° C. to about 200° C.

26. A process according to claim 16 wherein the medium contains an alkali metal hydroxide in the amount of at least about one mole to about 2 moles per mole of primary alcohol moiety undergoing conversion to carboxylic acid group.

27. A process according to claim 16 wherein the alkali metal hydroxide is sodium hydroxide.

28. A process according to claim 16 wherein the strong acid is hydrochloric acid or sulfuric acid.

29. A process according to claim 16 wherein the process is carried out in a batch reactor system.

30. A process according to claim 16 wherein the process is carried out in a continuous reactor system.

* * * * *